United States Patent [19]

Tsai

[11] 4,194,907
[45] Mar. 25, 1980

[54] GOLD ALLOYS FOR FUSION TO PORCELAIN

[75] Inventor: Min H. Tsai, Van Nuys, Calif.

[73] Assignee: Unitek Corporation, Monrovia, Calif.

[21] Appl. No.: 953,247

[22] Filed: Oct. 20, 1978

[51] Int. Cl.² .............................................. C22C 5/00
[52] U.S. Cl. .................... 75/134 N; 75/165; 75/172 G
[58] Field of Search ............... 75/134 R, 134 N, 165, 75/172 R, 172 G

[56] References Cited

U.S. PATENT DOCUMENTS

| | | | |
|---|---|---|---|
| 3,413,723 | 12/1968 | Wagner et al. | 32/8 |
| 3,472,653 | 10/1969 | Short | 75/165 |
| 3,667,936 | 6/1972 | Katz | 75/134 N |
| 3,804,616 | 4/1974 | Goltsov et al. | 75/134 N |
| 3,868,249 | 2/1975 | Hufford, Jr. et al. | 75/165 |
| 3,961,420 | 6/1976 | Tuccillo | 32/8 |
| 3,981,723 | 9/1976 | Tuccillo | 75/165 |
| 4,069,370 | 1/1978 | Harmsen et al. | 75/165 |

OTHER PUBLICATIONS

Williams, Jr. et al., "Porcelain-to-Metal Alloy Systems," *Dental Porcelain: The State of Art–1977*, University of Southern California School of Dentistry, Los Angeles, California, pp. 71–77.

*Primary Examiner*—L. Dewayne Rutledge
*Assistant Examiner*—Peter K. Skiff
*Attorney, Agent, or Firm*—Richard H. Brink; David J. Mugford

[57] ABSTRACT

A gold alloy for use in a dental restoration which does not cause discoloration and greening of dental porcelain after being cast and having a porcelain jacket fired thereon. The gold alloy also produces extremely clean castings. The alloy is 30–50% gold, 30–50% palladium, 5–30% silver, 0.01–5% of at least one element from silicon, boron, germanium and mixtures thereof and 0.01–1.0% of ruthenium. Other elements are included for strength.

22 Claims, No Drawings

GOLD ALLOYS FOR FUSION TO PORCELAIN

DESCRIPTION

BACKGROUND OF THE INVENTION

Noble-metal alloys, adapted for ceramic bonding (the application of a porcelain jacket or covering) are well known in dentistry and are used in the manufacturing of crowns, bridges and other prosthetic appliances. These so-called noble "ceramic alloys" typically consist of 80–90% gold, 5–15% platinum and 1–10% palladium. Alloys of this type, and application of the alloys in dentistry, are discussed in detail in U.S. Pat. No. 3,413,723—Wagner & Pralow issued Dec. 3, 1968 and for brevity the disclosure of this patent is incorporated herein by reference.

Due to the increase in price of gold and platinum, alloys with lower gold content were developed, (U.S. Pat. No. 3,667,936, and U.S. Pat. No. 3,981,723). These types of alloys consist essentially of 30–60% gold, 15–50% palladium, and 5–30% of silver. Platinum is limited in use or eliminated from these alloys. A major problem with these known alloys is that they tend to cause greening and discoloration of dental porcelains fused onto the understructure of these alloys, especially for the light shades of porcelains. Metallurgists hypothesize that greening of dental porcelain fused onto these alloys is caused by evaporation and redeposition of silver onto the porcelain or surface diffusion of silver and oxidation of silver or reaction of silver with sulfur during the ceramic firing. Although the exact mechanism is not entirely known, it has been recognized that greening and discoloration of dental porcelain is caused by silver in these alloys. The problem is discussed by R. V. Williams, Jr. et al in Dental Porcelain: The State of the Art-1977, Henry N. Yamada, editor, 1977, University of Southern California School of Dentistry, Los Angeles, California, pages 71–77 and in U.S. Pat. No. 3,667,936.

Coloration of porcelain may be limited by baking one layer of gold powder onto the understructure of the alloy prior to the application of dental porcelain; however, this technique increases cost (gold powder and labor), and causes uncertainty of bond strength. Another way to avoid this problem is the elimination of the use of silver in the alloy and increasing the usage of gold and palladium. This also increases the cost of the alloy.

By adding silicon, boron, germanium or a mixture thereof into the gold-palladium-silver system, I unexpectedly found that this alloy produced extremely clean castings, and this alloy did not cause greening and discoloration of dental porcelain. Addition of these elements in the gold-palladium-silver system caused hot tear in the casting but was eliminated by incorporating a small amount of ruthenium in the alloy.

Williams et al at page 74 of the above publication disclose that they have found traces of silicon in raw materials for gold-palladium base alloy systems but describe the undesirability of such material in the alloy without recognizing that the greening problem they discuss could be eliminated by incorporating a larger amount of silicon in the alloy.

SUMMARY OF THE INVENTION

This invention relates to a castable dental alloy suitable for fusing with dental porcelains and producing extremely clean castings. This alloy will not cause greening and discoloration of dental porcelain. This alloy is also lower in cost. The alloy includes 30–50% gold, 30–50% palladium, 5–30% silver, a sufficient amount of silicon, boron, germanium or a mixture thereof to prevent greening and discoloration of porcelain when fired thereon, and 0.01–1.0% of ruthenium. The amount of silicon, boron, germanium or mixtures thereof is in the range of 0.01%–5% depending upon the amount of silver in the alloy. The amount of such elements is directly proportional to the amount of silver in the alloy. Other elements such as indium and tin are included for strength of the alloy.

A presently preferred formulation of the alloy consists essentially of 43.0% gold, 42.0% palladium, 8.7% silver, 2.0% indium, 4.0% tin, 0.2% silicon and 0.1% ruthenium.

In method terms, the invention contemplates the technique of making a dental restoration by firing a porcelain jacket over a cast body of an alloy having the aforesaid characteristics and a method of preventing greening and discoloration of porcelain jackets fired on a gold-palladium-silver alloy system.

DESCRIPTION OF THE PREFERRED EMBODIMENT

The greening-free, silver containing ceramic alloy of this invention, has the following acceptable range, (percentages are by weight).

| Element | Acceptable Ranges (%) |
|---|---|
| gold | 30–50 |
| palladium | 30–50 |
| silver | 5–30 |
| indium | 0–10 |
| tin | 0–10 |
| silicon, boron, germanium or a mixture thereof | 0.01–5 |
| ruthenium | 0.01–1.0 |
| Other platinum family elements (for example rhodium, rhenium, iridium and osmium) | 0–3 |

The relatively high gold and palladium content, provide satisfactory corrosion resistance when the alloy is exposed to mouth fluids. Indium and tin are used to strengthen and to increase the hardness of the alloy. Gold, palladium and silver are the primary determinants of the thermal expansion property of the alloy, although the other components play some role in these characteristics. Silicon, boron and germanium are used to eliminate greening and discoloration of dental porcelain fused onto the understructure of this type of alloy.

Silicon, boron and germanium also contribute to the cleanness of casting, which is broken from the investment materials. Hot tear of the castings is eliminated by including ruthenium in the alloy. Gold, palladium and silver can be replaced by other platinum family elements (for example, rhodium, rhenium, iridium and osmium); up to 3% without significantly affecting the properties of alloy.

The components are alloyed by induction melting in an argon atmosphere. The alloy is rolled and cut into small wafers for remelting. Conventional techniques are used to make a finished dental restoration with the alloy. An investment mold is prepared by using the conventional lost-wax or burn-out plastic methods. The alloy is then melted and poured in the mold which is mounted in a centrifugal casting machine. After cooling, the mold is broken away and the casting cleaned, polished and finished in preparation for application of dental porcelains by the usual firing techniques.

The alloy has been tested and proved satisfactory with dental porcelain available from Vita Zahnfabrik under the trademark VMK-68. Other compatible porcelain materials are available from Dentsply International, Inc. (under the trademark "Biobond") and from the Ceramco Division of Johnson & Johnson.

Strength, elongation and modulus of elasticity are tested by using the Instron machine. Vickers hardness is obtained by testing specimens in a microhardness tester with a diamond indenter. All these tests are familiar to those skilled in the art. The Shell and Nielson technique (Shell, J. S. and Nielson, J. P., Journal of Dental Research 41, 1962 - P. P. 1424–1437) is used to determine the bond strength of porcelain to metal. Greening and discoloration of the dental porcelain is observed by fusing one of the light shades of porcelain, shade $A_1$ for example, onto the understructure of the alloy. The outstanding characteristic of this alloy is the maintenance of a greening and discoloration free dental porcelain fused onto this metal. Another important characteristic of this alloy is that castings made from the alloy are extremely clean when they are broken from the investment materials. A further advantage of this alloy is that it is relatively low in cost.

The following examples are intended to illustrate the invention claimed herein without unduly resticting it. A number of different alloys were tested in arriving at the preferred formulations and the acceptable component ranges. Typical examples of these alloys are set forth below (the components being designated in percentages by weight):

|  | Example 1 | Example 2 | Example 3 | Example 4 |
|---|---|---|---|---|
| gold | 32.5 | 32.3 | 43.0 | 40.0 |
| palladium | 45.0 | 45.0 | 42.0 | 42.0 |
| silver | 16.2 | 16.2 | 8.7 | 8.7 |
| indium | 2.0 | 2.0 | 2.0 | 2.0 |
| tin | 4.0 | 4.0 | 4.0 | 4.0 |
| silicon | 0.2 | 0.4 | 0.2 | 3.2 |
| ruthenium | 0.1 | 0.1 | 0.1 | 0.1 |

The alloy of Example 1 for comparison shows some greening in the porcelain jacket. By increasing silicon content from 0.2% to 0.4%, greening and discoloration of the porcelain jacket are not detected. Example 1 and Example 2 are higher in silver content and lower in gold content. Example 3 is higher in gold content and lower in silver content. Only 0.2% silicon in the alloy of Example 3 is able to avoid discoloration of dental porcelain. The alloy of Example 4 contains the upper limit of silicon content in the gold-palladium-silver system of that example. The alloys of Examples 1 through Example 4 produce extremely clean castings.

|  | Example 5 | Example 6 | Example 7 | Example 8 |
|---|---|---|---|---|
| gold | 40.0 | 39.0 | 39.0 | 39.0 |
| palladium | 45.0 | 44.0 | 44.0 | 44.0 |
| silver | 8.7 | 10.7 | 10.7 | 10.7 |
| indium | 2.0 | 2.0 | 2.0 | 2.0 |
| tin | 4.0 | 4.0 | 4.0 | 4.0 |
| silicon | 0 | 0 | 0.1 | 0.15 |
| boron | 0 | 0.2 | 0.1 | 0 |
| germanium | 0.2 | 0 | 0 | 0.05 |
| ruthenium | 0.1 | 0.1 | 0.1 | 0.1 |

The alloys of Examples 5 through Example 8 do not cause greening and discoloration of dental porcelain. The alloys include boron, germanium, silicon or a combination of the elements. The alloys of EXamples 6 through Example 8 produce particularly clean castings.

|  | Example 9 | Example 10 |
|---|---|---|
| gold | 44.0 | 44.0 |
| palladium | 42.0 | 42.0 |
| silver | 7.7 | 7.7 |
| indium | 1.0 | 5.0 |
| tin | 5.0 | 1.0 |
| silicon | 0.2 | 0.2 |
| ruthenium | 0.1 | 0.1 |

The alloys of Examples 9 and 10 have slight differences in hardness and strength. Both exhibit similar casting behavior and porcelain bonding characteristics. Both alloys do not cause greening of porcelain. The alloy of Example 9 has the following properties without heat treatment.

| Ultimate Tensile Strength | 69,000 psi |
|---|---|
| Yield Strength | 42,000 psi |
| Modulus of Elasticity | $18 \times 10^6$ psi |
| Elongation | 16% |
| Vickers hardness | 160 |
| Bond Strength | 12,000 psi |

|  | Example 11 | Example 12 | Example 13 |
|---|---|---|---|
| gold | 44.0 | 44.0 | 44.0 |
| palladium | 40.0 | 40.0 | 40.0 |
| silver | 7.7 | 7.7 | 7.7 |
| indium | 2.0 | 2.0 | 2.0 |
| tin | 4.0 | 4.0 | 4.0 |
| silicon | 0.2 | 0.2 | 0.2 |
| ruthenium | 0.1 | 0.1 | 0.1 |
| platinum | 2.0 | 0 | 1.6 |
| rhodium | 0 | 2.0 | 0 |
| rhenium | 0 | 0 | 0.4 |
| iridium | 0 | 0 | 0 |
| osmium | 0 | 0 | 0 |

|  | Example 14 | Example 15 |
|---|---|---|
| gold | 44.0 | 44.0 |
| palladium | 40.0 | 41.0 |
| silver | 7.7 | 7.7 |
| indium | 2.0 | 2.0 |
| tin | 4.0 | 4.0 |
| silicon | 0.2 | 0.2 |
| ruthenium | 0.1 | 0.1 |
| platinum | 1.60 | 0 |
| rhodium | 0 | 0 |
| rhenium | 0 | 0 |
| iridium | 0.4 | 0 |
| osmium | 0 | 1.0 |

All these examples showed that the elimination of greening of porcelain and maintenance of clean and sound castings were not affected by replacing palladium in part with other platinum family elements in the alloy.

While this invention has been described and exemplified in terms of its preferred embodiment, those skilled in the art will appreciate that modifications can be made without departing from the spirit and scope of this invention.

I claim:

1. A castable dental alloy suitable for bonding with dental porcelain comprising about 30–50% gold, 30–50% palladium, 5–30% silver, 0.01–1.0% ruthenium and a member selected from the groups consisting of silicon, boron, germanium and mixtures thereof in an amount sufficient to prevent greening and discoloration of porcelains when fired thereon.

2. The alloy defined in claim 1 containing about 0.01–5% of a member selected from the group consisting of silicon, boron, germanium and mixtures thereof.

3. The alloy defined in claim 2 further comprising elements for increasing the strength of said alloy.

4. A castable dental alloy suitable for bonding with dental porcelain without a green color after porcelain is fired on the cast alloy, consisting essentially of:
   gold: 30–50 percent;
   palladium: 30–50 percent;
   silver: 5–30 percent;
   indium: 0–10 percent;
   tin: 0–10 percent;
   ruthenium: 0.01–1.0 percent;
   other platinum family elements 0–3 percent, and;
   silicon, boron, germanium or a mixture thereof 0.01–5 percent.

5. The alloy defined in claim 4 formed as a cast body for intra-oral installation and further comprising a porcelain jacket fired on the body.

6. The alloy defined in claim 4 wherein the constituent elements consist essentially of:
   Gold: 32.3 percent;
   Palladium: 45.0 percent;
   Silver: 16.2 percent;
   Indium: 2.0 percent;
   Tin: 4.0 percent;
   Silicon: 0.4 percent;
   Ruthenium: 0.1 percent.

7. The alloy defined in claim 4 wherein the constituent elements consist essentially of:
   Gold: 43.0 percent;
   Palladium: 42.0 percent;
   Silver: 8.7 percent;
   Indium: 2.0 percent;
   Tin: 4.0 percent;
   Silicon: 0.2 percent;
   Ruthenium: 0.1 percent.

8. The alloy defined in claim 4 wherein the constituent elements consist essentially of:
   Gold: 40.0 percent;
   Palladium: 42.0 percent;
   Silver: 8.7 percent;
   Indium: 2.0 percent;
   Tin: 4.0 percent;
   Silicon: 3.2 percent;
   Ruthenium: 0.1 percent.

9. The alloy defined in claim 4 wherein the constituent elements consist essentially of:
   Gold: 40.0 percent;
   Palladium: 45.0 percent;
   Silver: 8.7 percent;
   Indium: 2.0 percent;
   Tin: 4.0 percent;
   Germanium: 0.2 percent;
   Ruthenium: 0.1 percent.

10. The alloy defined in claim 4 wherein the constituent elements consist essentially of:
    Gold: 39.0 percent;
    Palladium: 44.0 percent;
    Silver: 10.7 percent;
    Indium: 2.0 percent;
    Tin: 4.0 percent;
    Boron: 0.2 percent;
    Ruthenium: 0.1 percent.

11. The alloy defined in claim 4 wherein the constituent elements consist essentially of:
    Gold: 39.0 percent;
    Palladium: 44.0 percent;
    Silver: 10.7 percent;
    Indium: 2.0 percent;
    Tin: 4.0 percent;
    Silicon: 0.1 percent;
    Boron: 0.1 percent;
    Ruthenium: 0.1 percent.

12. The alloy defined in claim 4 wherein the constituent elements consist essentially of:
    Gold: 39.0 percent;
    Palladium: 44.0 percent;
    Silver: 10.7 percent;
    Indium: 2.0 percent;
    Tin: 4.0 percent;
    Silicon: 0.15 percent;
    Germanium: 0.05 percent;
    Ruthenium: 0.1 percent.

13. The alloy defined in claim 4 wherein the constituent elements consist essentially of:
    Gold: 44.0 percent;
    Palladium: 42.0 percent;
    Silver: 7.7 percent;
    Indium: 1.0 percent;
    Tin: 5.0 percent;
    Silicon: 0.2 percent;
    Ruthenium: 0.1 percent.

14. The alloy defined in claim 4 wherein the constituent elements consist essentially of:
    Gold: 44.0 percent;
    Palladium: 42.0 percent;
    Silver: 7.7 percent;
    Indium: 5.0 percent;
    Tin: 1.0 percent;
    Silicon: 0.2 percent;
    Ruthenium: 0.1 percent.

15. The alloy defined in claim 4 wherein the constituent elements consist essentially of:
    Gold: 44.0 percent;
    Palladium: 40.0 percent;
    Silver: 7.7 percent;
    Indium: 2.0 percent;
    Tin: 4.0 percent;
    Silicon: 0.2 percent;
    Ruthenium: 0.1 percent;
    Platinum: 2.0 percent.

16. The alloy defined in claim 4 wherein the constituent elements consist essentially of:
    Gold: 44.0 percent;
    Palladium: 40.0 percent;
    Silver: 7.7 percent;
    Indium: 2.0 percent;
    Tin: 4.0 percent;
    Silicon: 0.2 percent;
    Ruthenium: 0.1 percent;
    Rhodium: 2.0 percent.

17. The alloy defined in claim 4 wherein the constituent elements consist essentially of:
    Gold: 44.0 percent;
    Palladium: 40.0 percent;
    Silver: 7.7 percent;
    Indium: 2.0 percent;

Tin: 4.0 percent;
Silicon: 0.2 percent;
Ruthenium: 0.1 percent;
Platinum: 1.6 percent;
Rhenium: 0.4 percent.

18. The alloy defined in claim 4 wherein the constituent elements consist essentially of:
Gold: 44.0 percent;
Palladium: 40.0 percent;
Silver: 7.7 percent;
Indium: 2.0 percent;
Tin: 4.0 percent;
Silicon: 0.2 percent;
Ruthenium: 0.1 percent;
Platinum: 1.60 percent;
Iridium: 0.4 percent.

19. The alloy defined in claim 4 wherein the constituent elements consist essentially of:
Gold: 44.0 percent;
Palladium: 41.0 percent;
Silver: 7.7 percent;
Indium: 2.0 percent;
Tin: 4.0 percent;
Silicon: 0.2 percent;
Ruthenium: 0.1 percent;
Osmium: 1.0 percent.

20. The alloy defined in claim 6 formed as a cast body for intra-oral installation, and further comprising a porcelain jacket fired on the body.

21. The alloy defined in claim 7 formed as a cast body for intra-oral installation, and further comprising a procelain jacket fired on the body.

22. The alloy defined in claim 8 formed as a cast body for intra-oral installation, and further comprising a porcelain jacket fired on the body.

* * * * *